(12) United States Patent
Das et al.

(10) Patent No.: US 10,561,309 B2
(45) Date of Patent: Feb. 18, 2020

(54) METHODS AND APPARATUS FOR IMAGING AND 3D SHAPE RECONSTRUCTION

(71) Applicant: Massachusetts Institute of Technology, Cambridge, MA (US)

(72) Inventors: Anshuman Das, Brighton, MA (US); Ramesh Raskar, Palo Alto, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 244 days.

(21) Appl. No.: 15/849,559

(22) Filed: Dec. 20, 2017

(65) Prior Publication Data
US 2018/0168440 A1    Jun. 21, 2018

Related U.S. Application Data

(60) Provisional application No. 62/437,058, filed on Dec. 21, 2016.

(51) Int. Cl.
*G06K 9/00* (2006.01)
*A61B 1/227* (2006.01)
(Continued)

(52) U.S. Cl.
CPC ............ *A61B 1/227* (2013.01); *A61B 1/0669* (2013.01); *A61B 5/0082* (2013.01);
(Continued)

(58) Field of Classification Search
CPC ..... A61B 1/227; A61B 5/6817; A61B 1/0669; A61B 5/0082; A61B 5/0066;
(Continued)

(56) References Cited

U.S. PATENT DOCUMENTS 6,628,298 B1    9/2003   Debevec
8,593,643 B2    11/2013  Kim et al.
(Continued)

OTHER PUBLICATIONS

Bedard, N., et al., Light field otoscope design for 3D in vivo imaging of the middle ear; published in Biomedical Optics Express vol. 8, Issue 1, pp. 260-272 (Dec. 14, 2016).
(Continued)

*Primary Examiner* — Van D Huynh
(74) *Attorney, Agent, or Firm* — Stephen R. Otis

(57) ABSTRACT

An otoscope may project a temporal sequence of phase-shifted fringe patterns onto an eardrum, while a camera in the otoscope captures images. A computer may calculate a global component of these images. Based on this global component, the computer may output an image of the middle ear and eardrum. This image may show middle ear structures, such as the stapes and incus. Thus, the otoscope may "see through" the eardrum to visualize the middle ear. The otoscope may project another temporal sequence of phase-shifted fringe patterns onto the eardrum, while the camera captures additional images. The computer may subtract a fraction of the global component from each of these additional images. Based on the resulting direct-component images, the computer may calculate a 3D map of the eardrum.

4 Claims, 4 Drawing Sheets

(51) Int. Cl.
  *A61B 5/00* (2006.01)
  *G06T 7/50* (2017.01)
  *G06T 15/50* (2011.01)
  *G06K 9/46* (2006.01)
  *A61B 1/06* (2006.01)

(52) U.S. Cl.
  CPC .......... *A61B 5/6817* (2013.01); *G06K 9/4661* (2013.01); *G06T 7/50* (2017.01); *G06T 15/50* (2013.01); *A61B 5/0066* (2013.01); *A61B 2562/0233* (2013.01); *G06K 2209/401* (2013.01)

(58) Field of Classification Search
  CPC ... A61B 2562/0233; G06T 7/50; G06T 15/50; G06K 9/4661; G06K 2209/401
  USPC ......................................................... 381/128
  See application file for complete search history.

(56) References Cited

U.S. PATENT DOCUMENTS

| | | | |
|---|---|---|---|
| 8,811,767 B2 | 8/2014 | Veeraraghavan et al. | |
| 9,867,528 B1* | 1/2018 | Boppart | A61B 1/2275 |
| 2007/0285422 A1* | 12/2007 | Nayar | G06K 9/4661 |
| | | | 345/426 |
| 2009/0185191 A1* | 7/2009 | Boppart | A61B 5/0066 |
| | | | 356/479 |
| 2015/0219441 A1* | 8/2015 | Haitjema | G01B 11/0608 |
| | | | 356/630 |
| 2016/0027194 A1* | 1/2016 | Zuiderweg | G01B 11/2441 |
| | | | 345/440 |

OTHER PUBLICATIONS

Carr, J., et al., Using the shortwave infrared to image middle ear pathologies; published in Proceedings of the National Academy of Sciences of the United States of America (PNAS), Sep. 6, 2016; 113(36):9989-94. doi: 10.1073/pnas.1610529113 (Sep. 6, 2016).

Das, A., et al., A compact structured light based otoscope for three dimensional imaging of the tympanic membrane; published in Proceedings of SPIE, vol. 9303, Feb. 26, 2015.

Estrada, J., et al., Noise robust linear dynamic system for phase unwrapping and smoothing; published in Optics Express vol. 19, Issue 6, pp. 5126-5133 (Mar. 2011).

Flores-Moreno, J., et al., Holographic otoscope using dual-shot-acquisition for the study of eardrum biomechanical displacements; published in Applied Optics vol. 52, Issue 8, pp. 1731-1742 (Mar. 2013).

Gorthi, S., et al., Fringe projection techniques: Whither we are?; published in Optics and Lasers in Engineering, vol. 48, Issue 2, p. 133-140 (Feb. 2010).

Guo, H., et al., Least-squares fitting of carrier phase distribution by using a rational function in profilometry fringe projection; published in Optics Letters vol. 31, Issue 24, pp. 3588-3590 (Dec. 2006).

Hernandez-Montes, M., et al., Optoelectronic holographic otoscope for measurement of nano-displacements in tympanic membranes; published in Journal of Biomedical Optics, 14(3), 034023 (2009). doi:10.1117/1.3153898 (Jul. 2009).

Holroyd, M., et al., An analysis of using high-frequency sinusoidal illumination to measure the 3D shape of translucent objects; published in 2011 IEEE Conference on Computer Vision and Pattern Recognition (CVPR), 2011.

Nayar, S., et al., Fast separation of direct and global components of a scene using high frequency illumination; published in ACM Transactions on Graphics (TOG)—Proceedings of ACM SIGGRAPH 2006 TOG, vol. 25 Issue 3, Jul. 2006, pp. 935-944, ACM New York, NY, USA.

Nguyen, C., et al., Noninvasive in vivo optical detection of biofilm in the human middle ear; published in Proceedings of the National Academy of Sciences of the United States of America (PNAS) Jun. 2012, 109 (24) 9529-9534. https://doi.org/10.1073/pnas.1201592109 (Jun. 2012).

Nguyen, C., Non-Invasive Assessment of Bacterial Biofilm in the Middle Ear Using Low-Coherence Interferometry/Optical Coherence Tomography and Acoustic Measurements; published as PhD Dissertation, University of Illinois at Urbana-Champaign (2012).

Otsu, N., A Threshold Selection Method from Gray-Level Histograms; published in IEEE Transactions on Systems, Man, and Cybernetics ( vol. 9, Issue: 1, Jan. 1979).

Park, J., et al., Investigation of middle ear anatomy and function with combined video otoscopy-phase sensitive OCT; published in Biomedical Optics Express vol. 7, Issue 2, pp. 238-250 (Jan. 2016).

Servin, M., et al., The general theory of phase shifting algorithms; published in Optics Express vol. 17, Issue 24, pp. 21867-21881 (Nov. 2009).

Valdez, T., et al., Multiwavelength Fluorescence Otoscope for Video-Rate Chemical Imaging of Middle Ear Pathology; published in Analytical Chemistry, 2014, 86 (20), pp. 10454-10460, DOI: 10.1021/ac5030232, Publication Date (Web): Sep. 16, 2014.

Valdez, T., et al., Multi-color reflectance imaging of middle ear pathology in vivo; published in Analytical and Bioanalytical Chemistry, May 2015;407(12):3277-83. doi: 10.1007/s00216-015-8580-y (2015).

Wang, Z., Three-dimensional surface imaging by multi-frequency phase shift profilometry with angle and pattern modeling for system calibration; published in Measurement Science and Technology, vol. 27, No. 8 (Jul. 2016).

\* cited by examiner

METHODS AND APPARATUS FOR IMAGING AND 3D SHAPE RECONSTRUCTION

RELATED APPLICATIONS

This application claims the benefit of U.S. Provisional Application No. 62/437,058, filed Dec. 21, 2016 (the "Provisional Application"), the entire disclosure of which is herein incorporated by reference.

FIELD OF TECHNOLOGY

The present invention relates generally to imaging.

COMPUTER PROGRAM LISTING

The following computer program file is incorporated by reference herein: source_code.txt with a size of about 17 KB, created as an ASCII .txt file on Dec. 3, 2017.

BACKGROUND

"Eardrum" means the tympanic membrane of an ear.

"Ear canal" means the external acoustic meatus of an ear.

"Green spectrum" of light means 606 THz to 526 THz, which corresponds to wavelengths of 495 nm to 570 nm.

"Infrared spectrum" of light means 300 GHz to 430 THz, which corresponds to wavelengths of 700 nm to 1 mm.

The terms "lateral" and "medial" are used herein in their anatomical sense. For example, if A is "lateral" to B, then the shortest distance between A and the midsagittal plane is greater than the shortest distance between B and the midsagittal plane. A "lateral" exterior surface of an eardrum means an exterior surface of the eardrum that is located on a lateral side, instead of a medial side, of the eardrum. If A is "medial" to B, then the shortest distance between A and the midsagittal plane is less than the shortest distance between B and the midsagittal plane.

"Middle ear" means the portion of an ear that is medial to the tympanic membrane and lateral to the oval window of the cochlea. The "middle ear" includes the malleus, incus and stapes and the tympanic cavity. As used herein, the "middle ear" does not include the eardrum.

"Visible spectrum" of light means 790 THz to 430 THz, which corresponds to wavelengths of 400 nm to 700 nm.

Additional definitions are set forth in the Definitions section below.

SUMMARY

An otoscope may include an active light source that illuminates the eardrum and a camera that captures images of the eardrum.

Light returning from an eardrum to an otoscope may comprise two components: (a) a direct component and (b) a global component. The direct component may comprise light that reflects from the eardrum and then travels directly to the otoscope. The global component may comprise light that passes through the eardrum, then reflects from the middle ear, then passes through the eardrum again and then travels to the otoscope. The eardrum, which is translucent, may scatter the global component and cause the global component to be diffuse light.

In conventional otoscopes, the translucency of the eardrum creates at least two technological problems:

First problem: In conventional otoscopes, the direct component of light (comprising light that reflects directly back from the eardrum to the otoscope, without entering the middle ear) makes it difficult for a camera in the otoscope to acquire a high-quality image of the middle ear. This is because the direct component of the light is noise in the context of an image of the middle ear, since the direct component never enters the middle ear.

Second problem: In conventional otoscopes, the global component of light (comprising light that reflects from the middle ear through the eardrum and then travels to the otoscope) makes it difficult for a camera in the otoscope to acquire a high-quality 3D image of the eardrum. This is because the global component of the light is noise in the context of a 3D image of the eardrum.

In illustrative implementations of this invention, returning light (i.e., light that returns from an eardrum to an otoscope) is separated (e.g., computationally separated in post-processing) into a direct component and a global component. This global-direct separation solves both technological problems listed above.

The first technological problem listed above is noise in images of the middle ear, due to light reflecting directly back from the eardrum. This first problem is solved by calculating an image of the middle ear and eardrum, based on the global component—not the direct component—of the returning light. Put differently, the first technological problem may be solved by computationally removing the direct component, and calculating an image of the middle ear and eardrum based on the global component.

The second technological problem listed above is noise in a 3D image of the eardrum, due to light that reflects from the middle ear and that is diffusely scattered when passing through the eardrum. This second problem is solved by calculating a 3D image of the eardrum, based on the direct component—not the global component—of the returning light. Put differently, the second technological problem may be solved by computationally removing the global component, and calculating a 3D image of the eardrum based on the direct component.

In illustrative implementations of this invention, a wide variety of methods may be employed to separate global and direct components of the returning light. Likewise, in illustrative implementations, a wide variety of methods (such as phase-shifting profilometry) may be employed to determine the 3D shape of the eardrum.

In some implementations of this invention, an active light source in the otoscope may project a first set of phase-shifted fringe patterns onto the eardrum, one fringe pattern at a time, in a temporal sequence. A camera in the otoscope may capture a first set of images of the eardrum while the eardrum is illuminated by the first set of phase-shifted fringe patterns. A computer may perform a global-direct separation algorithm that calculates a global component of the first set of images. The computer may output the global component as an image of middle ear and eardrum. This image may show structures in the middle ear, such as the stapes and incus, and may also show the eardrum. Thus, the otoscope may "see through" the eardrum to visualize the middle ear. The active light source may project a second set of phase-shifted fringe patterns onto the eardrum, one fringe pattern at a time, in a temporal sequence. The camera may capture a second set of images while the eardrum is illuminated by the second set of phase-shifted fringe patterns. The computer may transform this second set of images into direct-component images by subtracting a fraction of the global component from each image in the second set of images. Based on the direct-component images, the computer may calculate a 3D map of the eardrum. This 3D map may specify 3D spatial coordinates of points on a lateral, exterior surface of the eardrum.

For example, in some implementations, each of the fringe patterns is sinusoidal spatial pattern. In some cases: (a) each fringe pattern in a subset of the fringe patterns varies in intensity in such a manner that intensity is a sinusoidal function of spatial position along an x-axis; and (a) each fringe pattern in another subset of the fringe patterns varies in intensity in such a manner that intensity is a sinusoidal function of spatial position along a y-axis, the x and y axes being perpendicular to each other.

In some cases, the otoscope is a hand-held instrument.

This invention has many practical uses. For example, in some implementations of this invention, the otoscope (and post-processing with the direct-global separation of light) may be employed to acquire an image of structures in the middle ear, or a 3D map of an eardrum, in order to aid in diagnosis of a clinical condition and in surgical planning. This, in turn, may reduce the use of x-ray CT scans (computed tomography scans), thereby saving some patients from the heavy dose of x-ray radiation associated with a CT scan.

This invention is not limited to otoscopes and to imaging of an ear. For example, this invention may be implemented as any type of endoscope that is configured to image any tissue or organ. For example, in some implementations, this invention may be implemented as a laparoscope (to image an abdomen or pelvis), cystoscope (to image a bladder), arthroscope (to image joints), nephroscope (to image a kidney), or bronchoscope (to image a lung). Also, for example, this invention may be implemented in industrial settings, as an imaging system that is configured: (a) to capture images of a translucent surface and objects behind the translucent surface; or (b) to reconstruct a 3D shape of the translucent surface.

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the description of this invention in the Field of Technology section is not limiting; instead it identifies, in a general, non-exclusive manner, a field of technology to which some implementations of this invention generally relate.

The above Figures show some illustrative implementations of this invention, or provide information that relates to those implementations. The examples shown in the above Figures do not limit this invention. This invention may be implemented in many other ways.

DETAILED DESCRIPTION

Hardware

Figure 1:
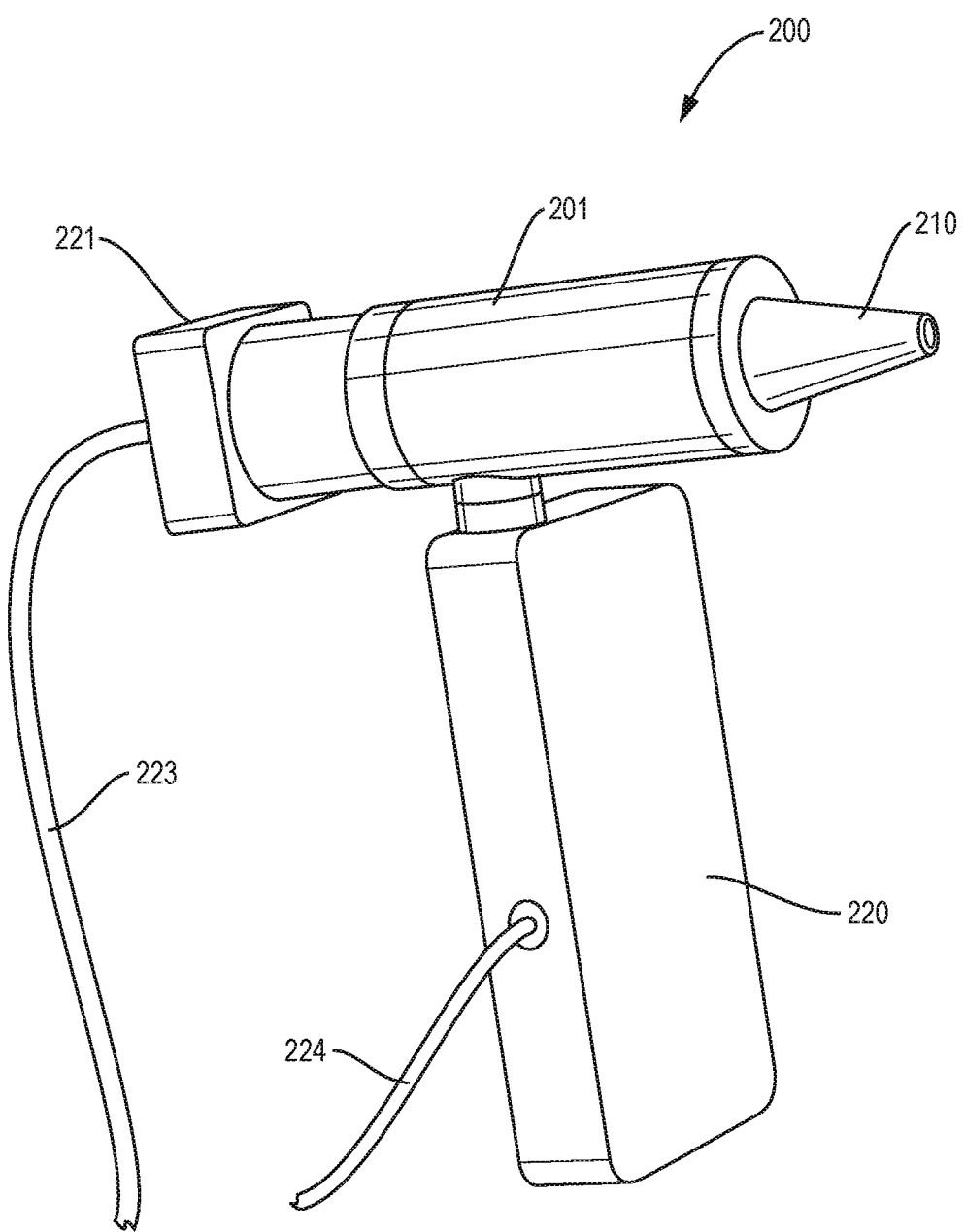
FIG. 1 shows a perspective view of an otoscope.

FIG. 1 shows a prospective view of an otoscope, in an illustrative implementation of this invention.

Figure 2:
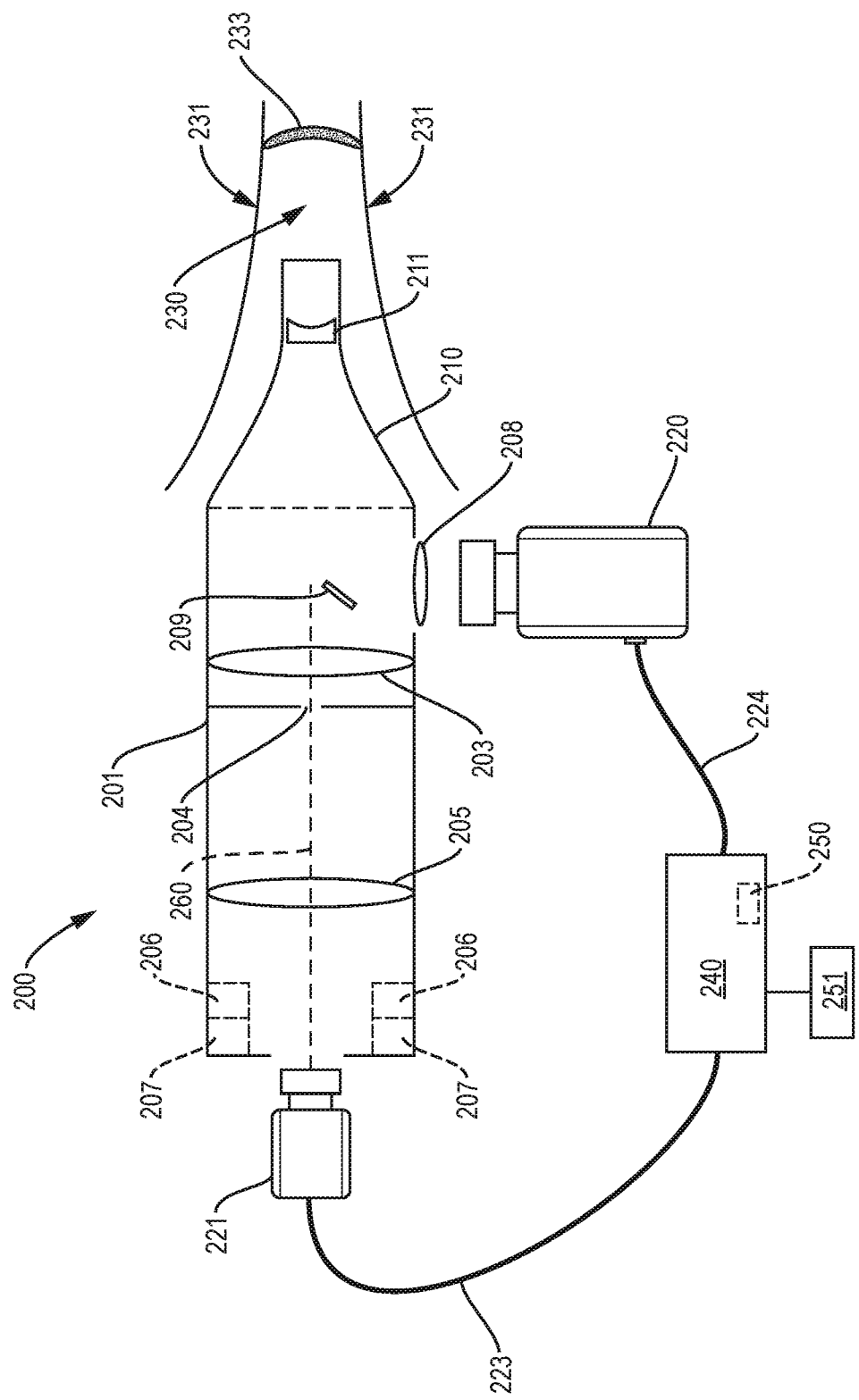
FIG. 2 is a diagram of an otoscope.

FIG. 2 is a diagram of an otoscope, in an illustrative implementation of this invention.

In the examples shown in FIGS. 1 and 2, an otoscope 200 includes a tube 201, a detachable speculum 210, a projector 220, a camera 221, a computer 240, USB (universal serial bus) cable 223, and HDMI (high-definition multimedia interface) cable 224. Computer 240 is shown in FIG. 2.

In the example shown in FIG. 2, speculum 210 is inserted into an ear canal 230, in such a way that speculum 210 is partially surrounded by the walls 231 of the ear canal 230. Projector 220 emits a temporal sequence of fringe patterns of light that reflect from front-surface mirror 209, pass through lens 211 and are projected onto eardrum 233. Speculum 210 includes a concave lens 211 that increases the field-of-view of camera 221 and that expands the light pattern emitted by projector 220. Speculum 210 is configured to be easily attached and detached from tube 201. For example, a threaded end of speculum 210 may be screwed around or into a threaded end of tube 201, or an elastic end of speculum 210 may be snapped into place relative to tube 201, or an elastic end of tube 201 may be snapped into place relative to speculum 210.

In the example shown in FIG. 2, tube 201 is attached to camera 221 and projector 220. Tube 201 also houses an opaque front-surface mirror 209, bi-convex lens 203, variable aperture 204, variable focus lens 205, extension rings 206, 207, and convex lens 208. Light emitted by the projector 220 passes through convex lens 208, then reflects from mirror 209, then passes through lens 211, and then travels to eardrum 233. Light returning from eardrum 233 (e.g., light that reflects directly from the eardrum or that reflects from the middle ear and passes through the eardrum) passes through lens 211, then through bi-convex lens 203, then through variable aperture 204, then through variable focus lens 205 and then travels to camera 221. Bi-convex lens 203 functions as a magnifier. Extension rings 206, 207 are positioned in such a way that they increase the distance between lens 205 and the image plane of camera 221. Convex lens 208 decreases the focal length of projector 220.

In the example shown in FIG. 2, mirror 209 and projector 220 are positioned, relative to tube 201 and camera 221, in such a way that light emitted by projector 220 is, immediately after reflecting from mirror 209, traveling in a direction that is not parallel to the optical axis 260 of camera 221 and is not parallel to the optical axis of tube 201. (In FIG. 2, the optical axis of tube 201 is identical to that of camera 221 and is also indicated by line 260.) Thus, light from projector 220 may, immediately after it reflects from mirror 209, be "off-axis" relative to the camera (e.g., by 5-10 degrees). This "off-axis" configuration may in turn facilitate triangulation to determine 3D position of points on an external lateral surface of the eardrum.

In FIG. 2, mirror 209 is opaque and has a reflective coating on its front surface (i.e., the surface of mirror 209 that is closest to speculum 210). An advantage of the front-surface mirror 209 is that the mirror reflects only a single reflection pattern. (In contrast, if a conventional mirror that reflects from its back side were used: (a) two reflection patterns would reflect from the mirror, one from the mirror's back side and the other from its front side; and (b) these two reflections would corrupt the images.). In FIG. 2, mirror 209 is positioned in such a manner that it does not block the optical axis 260 of camera 221.

Projector 220 may project high spatial frequency patterns of illumination. Projector 220 may include one or more active light sources, such as LEDs (light-emitting diodes). Projector 220 may also include a digital micromirror device.

The digital micromirror device may comprise an array of individually addressable micromirrors. The position of each micromirror in the array may be individually controlled by an actuator, which is turn controlled by a computer. The position of each micromirror may determine whether light reflecting from the micromirror is projected by the projector. For example, projector 220 may comprise a DLP (digital light processing) projector, a pico projector or any other projector that includes an array of mirrors that are individually steered by micro-electro-mechanical actuators.

This invention is not limited to an LED light source and digital micromirror device, for generating structured illumination patterns. In some alternative implementations, projector 220 comprises: (a) an LCD (liquid crystal display) projector; (b) a Michelson interferometer; (c) a fiber optic interferometer system with laser diode input; (d) grating projection system; (e) spatial light modulator; (f) diffractive optical element; or (g) super-luminescent diode with an acousto-optic tunable filter. In each of the examples listed in the preceding sentence, the projector may project high spatial frequency patterns of illumination (e.g., in some cases, phased-shifted fringe patterns) or other structured illumination.

In some implementations, it is desirable to capture images only in the green spectrum of light. This is because: (a) when illuminated by broadband white light, an eardrum may reflect light primarily in the green spectrum; (b) the eardrum and middle ear may have low reflectivity in the blue spectrum of frequencies, and (b) the red channel in an RGB image may capture vasculature or inflammation, making 3D reconstruction difficult. In illustrative implementations, capturing images in only the green spectrum of frequencies may be achieved in a variety of ways. For example, in some cases: (a) the projector projects broadband illumination in the visible spectrum, (b) only data from the green channel of an RGB image is utilized; and (c) data from the red and blue channels of the RGB image is disregarded. Alternatively, in some cases, the projector projects light that is predominantly or entirely in the green spectrum of frequencies. For example, in some alternative implementations, the FWHM band of frequencies (i.e., the band of frequencies in which the intensity of the projected light is equal to at least half of the maximum intensity of the projected light) may fall entirely in the green band of frequencies.

However, this invention is not limited to utilizing only data regarding light in the green spectrum. For example, in some implementations of this invention, the active light source(s) in the projector emit light in the visible spectrum or in the infrared spectrum. Likewise, in some implementations of this invention, data regarding light in the visible spectrum or infrared spectrum is captured by the camera and is taken as an input when calculating a global component of light or a direct component of light, or when calculating an image.

Variable focus lens 205 may adjust focal length to compensate for anatomical differences (e.g., differences in size of ear in different patients). In some cases, variable focus lens 205 may comprise a liquid lens. The shape and focal length of the liquid lens may be controlled by an applied electric field. In some cases, variable focus lens 205 may comprise a lens and an electromechanical actuator (e.g., e.g., electrical motor). The actuator may move the lens to different distances from the camera 221. In some cases, variable focus lens 205 may comprise a varifocal lens or parfocal lens. In some cases, the diameter of the variable aperture is electromagnetically or electro-mechanically controlled, or is manually controlled. In some cases, computer 240 outputs signals that control variable focus lens 205 and variable aperture 204 in such a way that changes in focal length and changes in aperture diameter are synchronized.

In the example shown in FIG. 2, computer 240: (a) controls projector 220, including controlling timing, shape, and orientation of light patterns emitted by projector 220 and including, in cases where the light patterns are spatially periodic, controlling spatial frequency and phase of the patterns; and (b) controls camera 221, including controlling timing of frames captured by camera 221. In addition, computer 240 receives data representing images captured by camera 221. Computer 220 may computationally (in post-processing) separate direct and global components of light measured by a camera. The direct component may comprise light that reflects from the eardrum 233 and travels directly to camera 221, without entering the middle ear. The global component may comprise light that has passed through the eardrum, reflected from the middle ear, then passed through the eardrum again, and then traveled to camera 221. Computer 240 may output an image of a global component. This image may show the eardrum and at least a portion of the middle ear (including incus and stapes) and the eardrum. Computer 240 may create direct-component images of the eardrum by subtracting, from images of the eardrum, a fraction of the global component. The computer 240 may take the direct-component images as an input and may calculate the 3D shape of a lateral exterior surface of the eardrum. Computer 240 may store data in, and access data stored in, memory device 250. Computer 240 may interface with I/O (input/output) devices 251. For example, the I/O devices 251 may comprise one or more of a keyboard, mouse, display screen, touch screen, microphone, and speaker. A human user may, via one or more of the I/O devices 251, input data or instructions to computer 240. Computer 240 may cause the one or more of the I/O devices 251 to output data in human readable format. For example, one or more of the I/O devices may comprise any type of display screen, including a video display screen, computer monitor screen, touch screen, television screen, head-mounted display, CRT (cathode ray tube) display, LED (light-emitting diode) display, PDP (plasma display panel), LCD (liquid crystal display), OLED (organic light-emitting diode) display, ELD (electroluminescent display), electronic paper or E ink. For example, the display screen may display an image of portions of a middle ear or eardrum. Likewise, the display screen may display a visual representation of a 3D map of a surface of an eardrum.

In the example shown in FIG. 1, otoscope 200 is configured to be held by only a single hand—or by both hands—of a human user while camera 221 captures images of eardrum 233. For example, the size and shape of projector 220 or tube 201 may be such that a human user may grasp projector 220 or tube 201 in a single hand—or in both hands at the same time. (For example, the user may hold otoscope 200 in one hand, while the user's other hand holds the patient's ear or adjusts the angle of the otoscope to visualize different sections of the eardrum.) Likewise, the weight of otoscope 200 may be sufficiently light that a single hand of a human user—or both hands of the user—may easily support the weight of the otoscope. In many cases, the patient may be sitting while camera 221 captures images of an eardrum of the patient. Alternatively, the otoscope may be supported by a stand, rather than the hand(s) of a human user, and the patient may lie supine with tilted head while a camera in the otoscope captures images of an eardrum of the patient.

This invention is not limited to the hardware shown in FIGS. 1 and 2. This invention may be implemented with any otoscope that includes a camera and a projector that is configured to project structured illumination.

The following paragraph describes a prototype of this invention.

In this prototype, the projector comprises an Altec Lansing® PJD 5134 DLP LED projector, with an 854×480 pixel resolution. The projector emits structured illumination. The structured illumination is steered through an otoscope head onto the eardrum. A front surface mirror steers light from the projector onto the eardrum. The front surface mirror minimizes multiple reflections. Reflected light from the eardrum is collected using a 25 mm lens arrangement with a variable focus and aperture (f/1.4-f/8). A camera with a resolution of 1280×720 pixels is coupled to the lens arrangement using a set of extender rings. The distance between the projector and the scene is set at 13 cm and the x-y calibration of the camera at that distance is 0.06 mm pixel to pixel spacing. The focal length of the otoscope may be initially set at 1 cm, but is variable within a range, to take into account anatomical variations. Triangulation is achieved by adjusting the angle between the optical axis of the camera and the projection system. The projector and lens assembly are housed in 3D-printed components.

The prototype described in the preceding paragraph is a non-limiting example of this invention. This invention may be implemented in many other ways.

Imaging the Eardrum and Middle Ear, Generally

Figure 3:
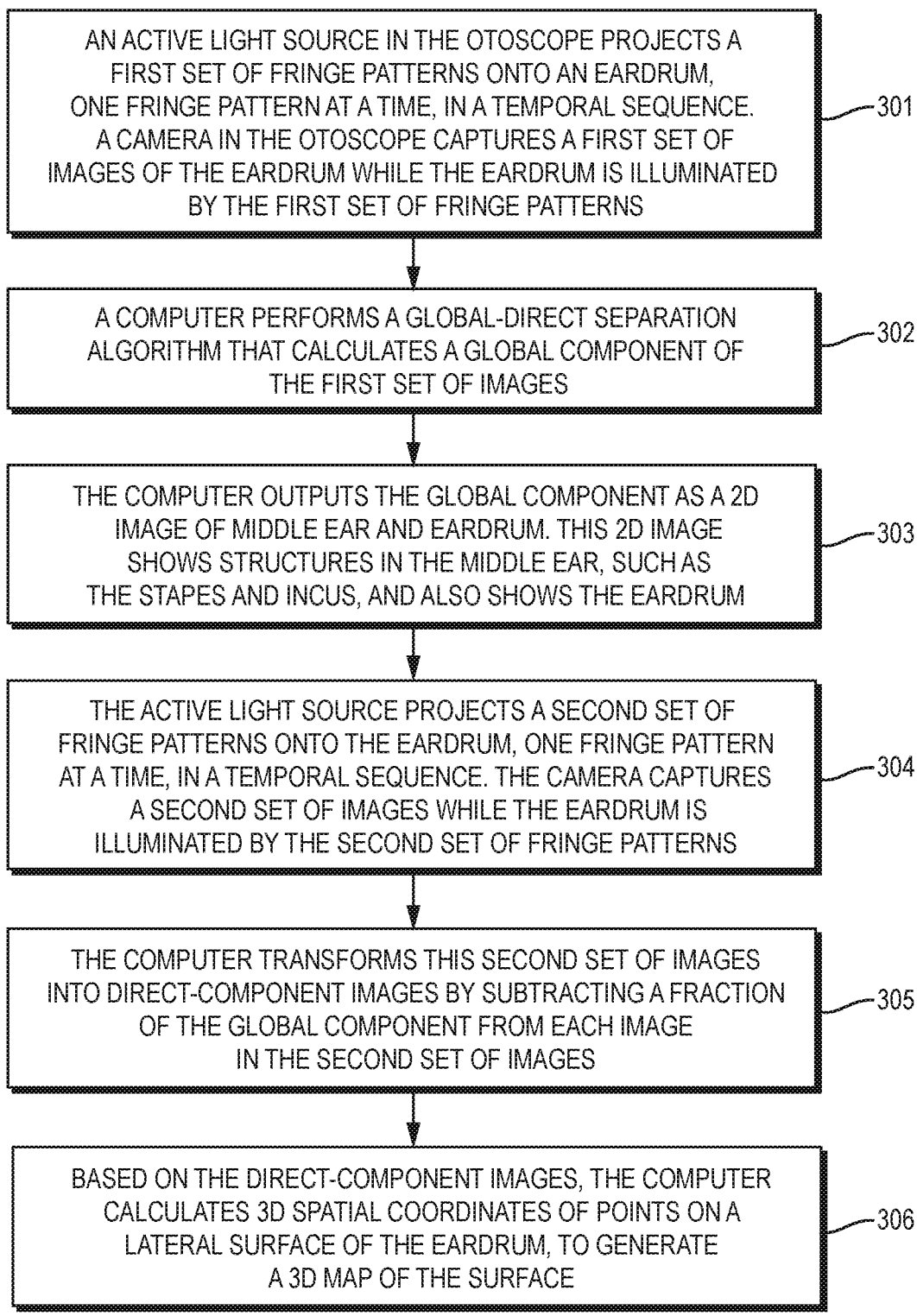
FIG. 3 is a flowchart for a method of imaging an eardrum and middle ear.

FIG. 3 is a flowchart of a method for imaging an eardrum and middle ear, in an illustrative implementation of this invention. In the example shown in FIG. 3, the method includes the following steps: An active light source in the otoscope projects a first set of fringe patterns onto an eardrum, one fringe pattern at a time, in a temporal sequence. A camera in the otoscope captures a first set of images of the eardrum while the eardrum is illuminated by the first set of fringe patterns (Step 301). A computer performs a global-direct separation algorithm that calculates a global component of the first set of images (Step 302). The computer outputs the global component as an image of middle ear and eardrum. This image shows structures in the middle ear, such as the stapes and incus, and also shows the eardrum (Step 303). The active light source projects a second set of fringe patterns onto the eardrum, one fringe pattern at a time, in a temporal sequence. The camera captures a second set of images while the eardrum is illuminated by the second set of fringe patterns (Step 304). The computer transforms this second set of images into direct-component images by subtracting a fraction of the global component from each image in the second set of images (Step 305). Based on the direct-component images, the computer calculates 3D spatial coordinates of points on a lateral surface of the eardrum, to generate a 3D map of the surface (Step 306).

In some implementations: (a) each fringe pattern is sinusoidal spatial pattern of illumination; (b) multiple subsets of the fringe patterns are projected on the eardrum; (c) for each subset, the fringe patterns in the subset are projected in a temporal pattern, one fringe pattern at a time; and (d) for each subset, the phase of each sinusoidal fringe pattern in the subset is shifted relative to the phase of at least one neighboring (in time) sinusoidal fringe pattern in the subset.

In some implementations of this invention: (a) a camera captures both a first set of images (for determining a global component) and a second set of images (for 3D shape reconstruction); and (b) post-processing (calculating a global component and 3D shape reconstruction) occurs entirely or partially after both the first and second sets of images are captured.

Figure 4:
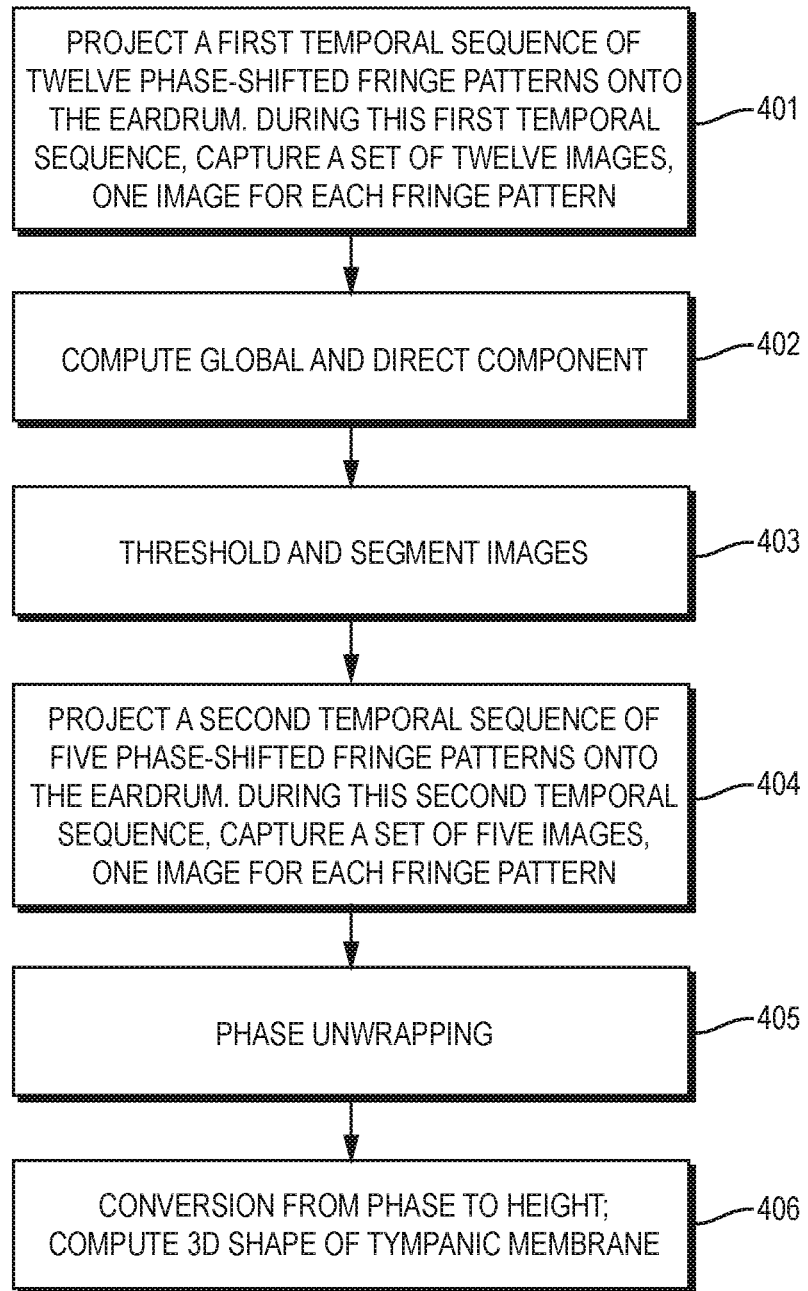
FIG. 4 is a flowchart for another method of imaging an eardrum and middle ear.

FIG. 4 is a flowchart for another method of imaging an eardrum and middle ear, in an illustrative implementation of this invention. In the example shown in FIG. 4, the method includes at least the following steps. Project a first temporal sequence of twelve phase-shifted fringe patterns onto the eardrum. During this first temporal sequence, capture a set of twelve images, one image for each fringe pattern (Step 401). Compute a global component and direct component of light (Step 402). Threshold and segment images (Step 403). Project a second temporal sequence of five phase-shifted fringe patterns onto the eardrum. During this second temporal sequence, capture a set of five images, one image for each fringe pattern (Step 404). Perform phase unwrapping (Step 405). Computationally convert phase to height. Calculate 3D shape of tympanic membrane (Step 406).

Illumination Patterns

In some implementations of this invention, a first set and second set of spatial fringe patterns of illumination are projected onto an eardrum in a temporal sequence, one fringe pattern at a time, and images of the eardrum are captured, one image for each fringe pattern in the sequence. Images of the first set of fringe patterns may be analyzed to determine a global component of light from the eardrum, and to output an image of global-component light that shows the middle ear and eardrum. Images of the second set of fringe patterns may be converted into direct-component images by subtracting a fraction of the global component, and may be analyzed to determine 3D spatial coordinates of points in the lateral exterior surface of the eardrum.

In some implementations, each fringe pattern is a sinusoidal spatial pattern. For example, in some cases: (a) a first set of projected fringe patterns (images of which are used to calculate a global component) comprises at least two subsets of fringe patterns; and (b) each subset comprises at least three fringe patterns.

In some implementations, in each subset of fringe patterns, the fringe patterns in the subset are phase-shifted relative to each other, with constant increments of phase between fringe patterns. For example: (a) a subset of fringe patterns may comprise a first fringe pattern, a second fringe pattern, and a third fringe pattern with constant increments of phase between them; (b) the phase of the second fringe pattern may be equal to the phase of the first fringe pattern plus $\pi/2$ radians; and (c) the phase of the third fringe pattern may be equal to the phase of the second fringe pattern plus $\pi/2$ radians.

This invention is not limited to phase increments of $\pi/2$ radians. For example, the constant phase increment for any subset or set of fringe patterns may be equal to $\pi/4$ radians, $\pi/3$ radian, $2\pi/3$ radians, or may be less than $\pi$ radians, or may be less than $2\pi$ radians.

This invention is not limited to sinusoidal fringe patterns. In illustrative implementations of this invention, a computer-controlled projector may project any kind of structured pattern of illumination unto an eardrum. For example, in some implementations of this invention, a projector may project, onto an eardrum, any or more of the following patterns: hexagonal grating, saw-tooth fringe pattern, triangular pattern, checkerboard pattern, any type of fringe pattern (including any fringe pattern used with an inverse analysis method), gray-code pattern, phase-shifted pattern, locally adapted projection pattern, optimal intensity-modulation pattern, time-multiplexed illumination patterns (e.g., binary codes, n-ary codes, gray code plus phase shifting), spatial neighborhood illumination codes (e.g., De Bruijn sequence, m-array) or direct coding pattern (e.g., grey levels, color). In some implementations, multiple projectors project patterns onto an eardrum.

Global-Direct Separation

In illustrative implementations of this invention, a computer analyzes images of the eardrum, to determine a global component of light returning from the eardrum. This global component may comprise light that reflects from the middle ear through the eardrum and then travels to the otoscope. A computer may output the global component as an image that shows the middle ear (including incus and stapes) and eardrum. The computer may save the global component, for later use. For example, the computer may later subtract a fraction of the global component from images of the eardrum, to generate images that represent a direct component of light from the eardrum. This direct component may comprise light that reflects directly back from the eardrum to the otoscope, without entering the middle ear.

In illustrative implementations of this invention, any method may be employed to separate direct and global components of light. For example, in some implementations of this invention, a Nayar Approach is employed to separate the direct and global components of light. As used herein: (a) "Nayar Approach" means any method or apparatus described in the Nayar Paper or the Nayar patent application; (b) "Nayar Paper" means Nayar, S., et al., *Fast Separation of Direct and Global Components of a Scene Using High Frequency Illumination*, ACM Transactions on Graphics, 25(3), 935-944, July 2006; and (c) "Nayar patent application" means U.S. Patent Publication 2007/0285422 A1, Nayar et al., Method of Separating Direct and Global Illumination in a Scene, published Dec. 13, 2007. Or, in some other implementations of this invention, a Kim Approach is employed to separate the direct and global components of light. As used herein: (a) "Kim Approach" means any method or apparatus described in the Kim patent; and (b) "Kim Patent" means U.S. Pat. No. 8,593,643 B2, issued Nov. 26, 2013, Kim et al., Methods and Apparatus for Direct-Global Separation of Light Using Angular Filtering. The entire disclosures of the Nayar Patent Application and Kim Patent are incorporated by reference herein.

In some implementations of this invention: (a) a projector projects high spatial frequency patterns of illumination onto an eardrum; (b) while the eardrum is illuminated by the patterns, a camera captures images of the eardrum; and (c) a computer calculates the global component of the images by employing the Nayar Approach.

Here are two non-limiting examples of "high spatial frequency" patterns that may be employed in this invention. In some cases, each projected illumination pattern is a spatially periodic pattern that has a spatial frequency of k spatial periods per millimeter of eardrum, where 0.2≤k≤4. In some cases, the smallest unit of the illumination pattern is projected by a patch of pixels in the projector and the number of pixels in the patch is: (a) less than $1 \times 10^{-4}$ of the total pixels in the projector; and (b) more than $1 \times 10^{-6}$ of the total pixels in the projector.

The following eleven paragraphs describe an approach that employs high-spatial frequency fringe patterns, in some implementations of this invention.

In this high-frequency fringe pattern approach, global light and direct light may be separated as follows: The eardrum may be illuminated with sinusoidal, high-spatial frequency fringe patterns of illumination in a temporal sequence, one pattern at a time. A camera may capture images of the eardrum, one image per fringe pattern. High frequencies may be observable in the reflection signal whereas low frequencies may be predominantly found in the global image. A light projector may project a set of cosine patterns of the form, $I=0.5 \cos(\omega+\delta_n)+0.5$ where, ω is the spatial frequency of the pattern, δn is the phase shift which was chosen to be in the set [−2π/3, 0, 2π/3], and n is a member of the set [−1,0,1]. The spatial frequency ω of the pattern may be large, and thus the image $I_n$ captured by the camera may be of the form $$I_n = \frac{1}{2}[L_d(x,y)\cos(\phi(x,y)+\delta_n)+L_d(x,y)+L_g(x,y)] \qquad \text{Eq. 1}$$

where $L_d(x,y)$ is the direct component and $L_g(x,y)$ is the global component, respectively. Note that $\phi(x,y)$ may encode depth information of the eardrum and depends on the spatial frequency and the arrangement of the projector and camera. From a set of at least three projections, the direct component $L_d(x,y)$ and the global component $L_g(x,y)$ may be decoupled from each other. Solving for $L_d(x,y)$ and $L_g(x,y)$ from Equation (1), we get, for a set of three images (one image for each fringe pattern):

$$L_g(x,y) = \frac{2}{3}(I_0(x,y)+I_1(x,y)+I_2(x,y))-L_d(x,y) \qquad \text{Eq. 2}$$

$$L_d(x,y) = \frac{2}{3}\sqrt{\frac{3(I_0(x,y)-I_2(x,y))^2 + }{(2I_1(x,y)-I_0(x,y)-I_2(x,y))^2}} \qquad \text{Eq. 3}$$

In this high-frequency fringe pattern approach, it is often desirable to project multiple subsets of phase-shifted spatial fringe patterns, and then average to minimize noise.

For example, in this high-frequency fringe pattern approach, the first set of fringe patterns (images of which are analyzed to separate direct and global components) may consist of a total of nine fringe patterns (three subsets, each subset consisting of three phase-shifted fringe patterns). For each of three subsets, respectively, the global component $L_g(x,y)$ may be calculated according to Equation 2. Then the three calculated values of $L_g(x,y)$ may be averaged, to determine an average value of the global component $L_g(x,y)$.

Alternatively, in this high-frequency fringe pattern approach, the first set of fringe patterns (images of which are analyzed to separate direct and global components) may consist of a total of twelve fringe patterns (four subsets, each subset consisting of three phase-shifted fringe patterns). For each of three subsets, respectively, the global component $L_g(x,y)$ may be calculated according to Equation 2. Then the three calculated values of $L_g(x,y)$ may be averaged, to determine an average value of the global component $L_g(x,y)$.

In this high-frequency fringe pattern approach, in the first set of fringe patterns (images of which are analyzed to separate direct and global components): (a) each subset of three fringe patterns may be identical to each other subset of three fringe patterns; or (b) at least one subset of three fringe patterns may differ (e.g., in orientation or spatial frequency or both) from at least one other subset of three fringe patterns.

For example, in this high-frequency fringe pattern approach: (a) the first set of fringe patterns (images of which are analyzed to separate direct and global components) may consist of a total of twelve fringe patterns (four subsets, each subset consisting of three phase-shifted fringe patterns); (b) the first subset of fringe patterns may consist of three x-axis sinusoidal patterns that are phase-shifted relative to each other and that have a spatial frequency A; (c) the second subset of fringe patterns may consist of three x-axis sinusoidal patterns that are phase-shifted relative to each other and that have a spatial frequency B, where B is larger than A; (d) the third subset of fringe patterns may consist of three y-axis sinusoidal patterns that are phase-shifted relative to each other and that have a spatial frequency A; (e) the fourth subset of fringe patterns may consist of three y-axis sinusoidal patterns that are phase-shifted relative to each other and that have a spatial frequency B; and (f) each of the first, second, third, and fourth subsets may consist of three fringe patterns (specifically, a first fringe pattern, second fringe pattern and third fringe pattern), the second fringe pattern being shifted in phase relative to the first fringe pattern and the third fringe pattern being shifted in phase relative to the second fringe pattern. As used herein: (a) an "x-axis sinusoidal pattern" is a spatial pattern of illumination in which intensity of illumination is a sinusoidal function of spatial position along a Cartesian x-axis; (b) a "y-axis sinusoidal pattern" is a spatial pattern of illumination in which intensity of illumination is a sinusoidal function of spatial position along a Cartesian y-axis; and (c) the x-axis and y-axis are perpendicular to each other.

Alternatively, in this high-frequency fringe pattern approach, the number of fringe patterns in each subset of fringe patterns may be greater than three.

In this high-frequency fringe pattern approach, a direct component of light may be computed according to Equation 3 for each of multiple subsets of images of fringe patterns, and an average direct component may be calculated.

After the global component has been computed, a computer may apply thresholding and segmentation to the global-component image. For example, a computer may perform thresholding and segmentation to remove portions (e.g., edges) of images that do not include useful information.

After this automatic thresholding and segmentation, a computer may output a global component image that shows the middle ear (including incus and stapes) and eardrum. The computer may save the global component, for later use. For example, the computer may later subtract a fraction of the global component from images of the eardrum, to generate images that represent a direct component of light from the eardrum. This direct component may comprise light that reflects directly back from the eardrum to the otoscope, without entering the middle ear.

The approach described in the preceding eleven paragraphs is a non-limiting example of a method of global-direct separation that may be employed in this invention. Other methods of global-direct separation (including other methods that involve projecting phase-shifted, high-spatial frequency patterns of illumination on the eardrum, or projecting other patterns of structured illumination on the eardrum) may be employed in this invention.

3D Shape Reconstruction of Eardrum

In illustrative implementations of this invention, a set of direct-component images of an eardrum (from which the global component has been subtracted) are employed to reconstruct the 3D shape of an eardrum.

For example, a camera may capture a set of images of an eardrum while the eardrum is illuminated with a temporal sequence of spatial illumination patterns. A computer may subtract a fraction of a global component from each of these images, to generate direct-component images of the eardrum. The global component may earlier have been extracted from a different set of images of the eardrum, and stored (see discussion above). A computer may, based on the direct-component images, calculate the 3D spatial position of points on a lateral surface of the eardrum, to generate a 3D map of the lateral surface of the eardrum. As noted above: (a) the global component may comprise light that reflects from the middle ear through the eardrum and then travels to the otoscope of light; and (b) the direct component may comprise light that reflects directly back from the eardrum to the otoscope, without entering the middle ear.

In some implementations of this invention, fringe projection profilometry is employed to recover 3D shape of the eardrum from direct-component images. The fringe projection profilometry may include the following steps: (a) projecting structured illumination (e.g., sinusoidal fringe patterns) on an eardrum; (b) capturing images of the eardrum while it is illuminated by the structured illumination (and the projected fringe pattern is deformed by, and phase-modulated by, the depth distribution of the eardrum relative to the camera); (c) transforming these images into direct-component images, by subtracting a fraction of a global component; (d) calculating the phase-modulation in the direct-component images by performing fringe analysis (e.g., Fourier transform method, phase stepping method or spatial phase detection method); (e) performing phase unwrapping, to calculate an unwrapped, continuous phase distribution proportional to depth of points in the eardrum, relative to the camera; and (e) mapping the unwrapped phase distribution to 3D spatial coordinates of points in the eardrum.

In illustrative implementations of this invention, any type of fringe analysis may be employed to reconstruct, from direct-component images, a 3D shape of an eardrum. For example, in some cases, the fringe analysis may comprise one or more of the following methods: wavelet transform (e.g., one- or two-dimensional wavelet transform), S-transform, dilating Gabor transform, Fourier transform, interpolated Fourier transform, regressive Fourier transform, windowed Fourier transform, multi-scale windowed Fourier transform, discrete-cosine transform, modified Hilbert transform, neural network, phase locked loop, regularized phase tracking, spatial phase detection, phase-shifting methods, spatial fringe analysis, temporal fringe analysis, or fringe analysis employing an inverse cosine function.

In some implementations of this invention, a computer analyzes direct-component images of an eardrum and calculates a so-called "wrapped" phase that is limited to a range of $2\pi$ radians (e.g., to the interval $[+\pi, -\pi]$ radians) and that thus creates phase discontinuities (of approximately $2\pi$ radians) between some neighboring pixels.

The computer may perform "phase unwrapping" by calculating, for each pixel (in a direct-component image), the integer multiple of $2\pi$ to be added to the wrapped phase of the pixel to produce an "unwrapped phase" of the pixel that eliminates phase discontinuities (of approximately $2\pi$ radians) between the pixel and its neighbors and that corresponds to the actual depth of the pixel. If there is no phase discontinuity (of approximately $2\pi$ radians) between the pixel and its neighbors, then the integer multiple may be zero.

In some implementations of this invention, any method of phase unwrapping may be employed. For example, in some cases, a computer may, for each given pixel of a direct-component image, compare phase at neighboring pixels and, if there is a phase discontinuity (of approximately $2\pi$ radians) between the given pixel and a neighboring pixel, add or subtract $2\pi$ to eliminate the phase discontinuity. Or, for example, in some implementations of this invention, a computer performs one or more of the following phase unwrapping algorithms: Ghiglia least-squares (weighted or unweighted), mask cut, region growing phase unwrapping, PEARLS (phase estimation using adaptive regularization with local smoothing), preconditioned conjugate gradient, Flynn's algorithm, multilevel quality guided phase unwrapping, quality guided path, temporal phase unwrapping, flood fill, Goldstein's algorithm, local histogram-based phase unwrapping, multi-level Lp-norm, Z πM algorithm, multi-grid, and weighted multi-grid.

In some implementations, the "unwrapped" phase that is extracted from a direct-component image comprises the sum of carrier-related phase and phase due to the eardrum's depth. A computer may computationally remove the carrier-related phase from the unwrapped phase. For example, in some implementations, a linear approach (such as plane-fitting, spectrum-shift, or average-slope) is employed to remove the carrier-related phase from the unwrapped phase. Or, in some cases, a non-linear approach (such as series-expansion, reference-subtraction, or phase-mapping) is employed to remove the carrier-related phase from the unwrapped phase.

In illustrative implementations, unwrapped phase may be mapped to 3D spatial coordinates of points on a lateral surface of an eardrum, to produce a 3D map of the eardrum. The mapping may be determined by prior calibration. In illustrative implementations, any method of calibration (e.g., linear calibration or non-linear calibration) may be employed to determine a mapping between unwrapped phase and depth of points on an eardrum.

The following eight paragraphs describe an approach—which is employed in some implementations of this invention—of reconstructing a 3D shape of an eardrum, based on direct-component images (from which a fraction of a global component has been subtracted).

In this 3D reconstruction approach, a projector projects a temporal sequence of five sinusoidal fringe patterns unto an eardrum, one fringe pattern at a time. The second, third, fourth and fifth (in temporal order) fringe patterns are each shifted by a constant phase increment relative to the immediately preceding (in temporal order) fringe pattern in the sequence. A camera captures five images of the eardrum while these five phase-shifted fringe patterns illuminate the eardrum, one image per fringe pattern.

In this 3D reconstruction approach, in some cases: (a) five fringe patterns are projected, one fringe pattern per 0.3 seconds for a total of 1.5 seconds; and (b) while each pattern, respectively, is projected, an image (e.g., $I_n(x,y)$ in Equation 4) is captured. The intensity of the five captured images may be modeled as:

$$I_n(x, y) = a(x, y) + b(x, y)\cos\left(\phi(x, y) + \omega_x x + \omega_y y + \frac{\pi}{2}n\right) \quad \text{Eq. 4}$$

for n=1, 2, 3, 4, 5; where $a(x,y)$ is the background intensity, $b(x,y)$ is the contrast, $\phi(x,y)$ is the modulated range and $(\omega_x,\omega_y)$ is the fringe pattern frequency, and the phase shift at each stage is π/2 radians.

In this 3D reconstruction approach, the camera may capture an image area larger than the region of the eardrum that is illuminated with the fringe pattern. A computer may perform thresholding (to determine which regions of the image meet a threshold of intensity of illumination) and may perform segmentation (to select regions of the image in which fringe patterns are visible). This automatic thresholding and segmentation may reduce noise due to stray light from regions that are dimly illuminated or illuminated by light other than direct illumination from fringe patterns.

After this automatic thresholding and segmentation, a fraction of a global component $L_g(x,y)$ that was previously computed is subtracted from the each of the phase-shifted images, $I_n(x,y)$, thereby producing direct-component images. The fraction is dependent on the scene and may be selected by trial and error. For example, in some cases, the fraction is greater than or equal to 0.1 and less than or equal to 0.4. In some other cases, the fraction is (a) less than 0.8 and greater than or equal to 0.6; (b) less than 0.6 and greater than or equal to 0.4; (c) less than 0.4 and greater than or equal to 0.2; or (d) less than 0.2 and greater than or equal to 0.01. In some use scenarios, the more diffuse the surface being imaged, the larger the fraction of the global component that is subtracted.

In this 3D reconstruction approach, after the fraction of the global component is subtracted from each image, the five images are computationally combined as follows:

$$f(x,y)=2I_3(x,y)-I_1(x,y)-I_5(x,y)+i[I_2(x,y)-I_4(x,y)] \quad \text{Eq. (5)}$$

where $i=\sqrt{-1}$. Equation (5) may be expressed as a complex output of a 5-step quadrature filter that is tuned at π/2 radians.

In this 3D reconstruction approach, a computer performs a phase unwrapping algorithm described in Estrada, J., et al., *Noise robust linear dynamic system for phase unwrapping and smoothing*, Optics Express, Vol. 19, No. 16 (March 2011). This phase-unwrapping algorithm involves a linear, dynamic, first-order feedback system.

In this 3D reconstruction approach, a computer computationally applies a low pass Gaussian filter (which filters out high spatial frequencies in the reconstructed 3D surface of the eardrum). Many structures in the eardrum are smooth and thus have a low spatial frequency. Thus, in many cases, it is desirable to employ a low-pass filter (e.g., a low-pass Gaussian filter) to remove high frequency content from the image.

In this 3D reconstruction approach, height (or equivalently, depth relative to camera) of points on a surface of an eardrum is estimated from phase, based on prior calibration. The height $h(x,y)$ may be calibrated using a conventional linear calibration procedure for phase profilometry, such as:

$$h(x, y) = \frac{L_0\Delta\phi(x, y)}{\Delta\phi(x, y) + 2\pi f_0 d} \quad \text{Eq. (6)}$$

where $L_0$ is the object camera distance, d is the distance between the camera and projector, $f_0$ is the spatial frequency of the projected pattern, and $\Delta\phi(x,y)$ is a relative change of phase in the eardrum. An example of a relative change in phase is a difference in phase between light that reflects from a depressed (more medial) point in the eardrum (e.g., umbo) and light that reflects from a "higher" (more lateral) point in the eardrum. A computer may convert from relative phase change $\Delta\phi(x,y)$ to height $h(x,y)$.

The approach described in the preceding eight paragraphs is a non-limiting example of a method of 3D reconstruction that may be employed in this invention. Other methods of 3D reconstruction (including other methods that involve projecting phase-shifted, high-spatial frequency patterns of illumination on the eardrum, or projecting other patterns of structured illumination on the eardrum) may be employed in this invention. In some implementations of this invention, any type of 3D shape reconstruction (e.g. 3D shape reconstruction based on triangulation) may be employed.

In some implementations, it is desirable to project as many spatial illumination patterns as possible, before too much movement of the otoscope relative to the eardrum occurs. For example, this movement may be due to the patient's head (and thus eardrum) changing position, or may be due to hand(s) of the user moving, if the user is holding the otoscope in his or her hand(s). Increasing the number of fringe patterns that are projected (and number of images captured) tends—all other factors being equal—to achieve better global direct separation as well as better 3D reconstructions. However, as the number of fringe patterns/images increases, the amount of time that it takes to project the patterns and capture the images also increases, all other factors being equal. As the amount of time increases, the amount of movement of the otoscope relative to the eardrum tends to increase, and this increased movement tends to introduce errors into 3D surface reconstruction and to create noise in averaged images (e.g., an averaged, global-component image).

For example, in a prototype of this invention: (a) the maximum rate at which a camera/projector system in the otoscope projects fringe patterns and captures images is approximately one camera frame (and one projected fringe pattern) per 0.1 second; and (b) thus the system may capture up to 20 frames in two seconds, without too much distortion due to movement of the otoscope relative to the eardrum. This prototype is a non-limiting example of this invention.

In some implementations, a GPU (graphics processing unit) is employed to increase the rate at which images are captured and patterns are projected. The GPU may facilitate capturing several hundred frames within 2 seconds, which may significantly improve the 3D shape reconstruction.

In some implementations, movement of the otoscope relative to the head may be reduced. For example: (a) the patient (whose eardrum is being imaged) may lie supine with the patient's head tilted and resting on a support, in order to reduce movement of the patient's head and thus movement of the patient's eardrum; and (b) the otoscope may be supported by a stand, tripod or other mechanical support (instead of by a hand or hands of a user), thereby avoiding movement that would occur if the otoscope were supported by a hand or hands of a user. Reduced movement of the otoscope relative to the patient's head may allow more fringe patterns to be projected (and more images to be captured) before too much movement occurs.

Software

In the Computer Program Listing above, a computer program file (source_code) is listed. This computer program files comprises software employed in a prototype implementation of this invention. To run this as a Matlab™ software file, the filename extension for it would be changed from ".txt" to a ".m" filename extension. This invention is not limited to the software set forth in the source_code computer program file. Other software may be employed. Depending on the particular implementation, the software used in this invention may vary.

Computers

In illustrative implementations of this invention, one or more computers (e.g., servers, network hosts, client computers, integrated circuits, microcontrollers, controllers, field-programmable-gate arrays, personal computers, digital computers, driver circuits, or analog computers) are programmed or specially adapted to perform one or more of the following tasks: (1) to control the operation of, or interface with, hardware components of an imaging system (e.g., an otoscope or endoscope), including any camera, projector, variable focus lens, variable aperture, or actuator that is configured to move any aperture or lens; (2) to control spatial illumination patterns (e.g., a temporal sequence of phase-shifted sinusoidal fringe patterns) projected onto a surface; (3) to control timing of images captured by a camera; (4) to calculate a global component of light from an eardrum, to output the global component as an image, and to store the global component; (5) to threshold and segment images; (6) to subtract a fraction of a global component from an image; (7) to perform phase profilometry calculations, including calculating unwrapped phase, performing phase unwrapping, and removing a carrier-related phase component; (8) to calculate a height (depth) distribution of points on a surface, based on calibration data; (9) to accept and store calibration data; (10) to receive data from, control, or interface with one or more sensors; (11) to perform any other calculation, computation, program, algorithm, or computer function described or implied herein; (12) to receive signals indicative of human input; (13) to output signals for controlling transducers for outputting information in human perceivable format; (14) to process data, to perform computations, and to execute any algorithm or software; and (15) to control the read or write of data to and from memory devices (items 1-15 of this sentence referred to herein as the "Computer Tasks"). The one or more computers (e.g. 240) may, in some cases, communicate with each other or with other devices: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied herein. For example, in some cases, instructions encoded in a tangible, non-transitory, computer-accessible medium comprise instructions for a computer to perform the Computer Tasks.

Network Communication

In illustrative implementations of this invention, electronic devices (e.g., 220, 221, 240) are configured for wireless or wired communication with other devices in a network.

For example, in some cases, one or more of these electronic devices each include a wireless module for wireless communication with other devices in a network. Each wireless module may include (a) one or more antennas, (b) one or more wireless transceivers, transmitters or receivers, and (c) signal processing circuitry. Each wireless module may receive and transmit data according to one or more wireless standards.

In some cases, one or more of the following hardware components are used for network communication: a computer bus, a computer port, network connection, network interface device, host adapter, wireless module, wireless card, signal processor, modem, router, cables or wiring.

In some cases, one or more computers or other electronic devices (e.g., 240, 220, 221) are programmed for communication over a network. For example, in some cases, one or more computers or other devices are programmed for network communication: (a) according to the Internet Protocol Suite, or (b) according to any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Definitions

More definitions are set forth above.

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

To say that a calculation is "according to" a first equation means that the calculation includes (a) solving the first equation; or (b) solving a second equation, where the second equation is derived from the first equation. Non-limiting examples of "solving" an equation include solving the equation in closed form or by numerical approximation or by optimization.

To compute "based on" specified data means to perform a computation that takes the specified data as an input.

To capture an image "by a camera" or "with a camera" means that the camera captures the image.

Here are some non-limiting examples of a "camera": (a) a digital camera; (b) a digital grayscale camera; (c) a digital color camera; (d) a video camera; (e) a light sensor or image sensor, (f) a set or array of light sensors or image sensors; (g) an imaging system; (h) a light field camera or plenoptic camera; (i) a time-of-flight camera; and (j) a depth camera. A camera includes any computers or circuits that process data captured by the camera.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

"Digital image" means digital data that encodes a visual image.

To "display" a digital image means to display a visual image that is perceptible to a human and that is encoded by the digital image.

For an event to occur "during" a time period, it is not necessary that the event occur throughout the entire time period. For example, an event that occurs during only a portion of a given time period occurs "during" the given time period.

The term "e.g." means for example.

Each equation above is referred to herein by the equation number set forth to the right of the equation. For example: "Equation (1)" means Equation (1) above. Non-limiting examples of an "equation", as that term is used herein, include: (a) an equation that states an equality; (b) an inequation that states an inequality (e.g., that a first item is greater than or less than a second item); (c) a mathematical statement of proportionality or inverse proportionality; and (d) a system of equations.

The fact that an "example" or multiple examples of something are given does not imply that they are the only instances of that thing. An example (or a group of examples) is merely a non-exhaustive and non-limiting illustration.

Unless the context clearly indicates otherwise: (a) a "fraction" means a positive number that is less than 0.9 and greater than zero; and (b) a "fraction" of Y means the product of m and Y, where $0 < m < 0.9$.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"For instance" means for example.

In the context of an imaging system that captures an image of a scene: (a) to say that B is in "front" of C means that B is optically closer to the scene than C is; and (b) to say that B is "behind" C means that B is optically farther from the scene than C is.

"G-component" means light that passes through an eardrum, reflects from a middle ear, passes through the eardrum again, and is measured by a camera.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

An "image" of X means an image that includes an image of all or part of X. For example, an "image" of an eardrum includes an image of all of part of the eardrum and may also include an image of other things (such as all or part of the middle ear or of walls of the ear canal).

A component of light "of" an image means a component of the light that was measured by a camera and is depicted in the image.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

To "integrate" means either (a) to perform integration in the calculus sense, or (b) to compute a sum of discrete samples.

"Intensity" means any measure of intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure, radiant energy density, luminance or luminous intensity.

Non-limiting examples of a "lens" are a single lens, compound lens or system of lenses.

"Light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

"ON" and "OFF", in the context of a binary value, are the two permitted states of the value, one state being "ON" and the other state being "OFF".

To project a pattern of illumination "onto an eardrum" means to project, from a position that is lateral to the eardrum, the pattern of illumination onto a lateral surface of the eardrum.

To say that B is "optically closer" to a scene than C is, means that the optical distance between B and the scene is less than the optical distance between C and the scene.

To say that B is "optically farther" from a scene than C is, means that the optical distance between B and the scene is more than the optical distance between C and the scene.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

To say that a temporal sequence of spatial illumination patterns is "phase-shifted" means that, for each respective pattern in the sequence (except the last pattern in the sequence), the phase of the respective pattern is different than the phase of the next pattern in the sequence.

As used herein, the term "set" does not include a group with no elements.

Non-limiting examples of a "sinusoidal" function include a sine function and a cosine function.

Unless the context clearly indicates otherwise, "some" means one or more.

A "spatial pattern of illumination" means a pattern of illumination that varies as a function of spatial position.

As used herein, a "subset" of a set consists of less than all of the elements of the set.

The term "such as" means for example.

To say that a machine-readable medium is "transitory" means that the medium is a transitory signal, such as an electromagnetic wave.

"3D" means three-dimensional.

A "3D map" (or "3D digital image" or "3D" image") of X means digital data that encodes 3D spatial coordinates of multiple points of X. For example, a "3D map" of a surface of an eardrum is digital data that encodes 3D spatial coordinates of multiple points of the surface.

"2D" means two-dimensional.

"X-axis sinusoidal pattern" is defined above.

As used herein, an "x axis" and "y axis" are each a Cartesian coordinate axis and are perpendicular to each other.

"Y-axis sinusoidal pattern" is defined above.

A matrix may be indicated by a bold capital letter (e.g., D). A vector may be indicated by a bold lower-case letter (e.g., α). However, the absence of these indicators does not indicate that something is not a matrix or not a vector.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; (7) one or more steps occur simultaneously, or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) projecting a first set of illumination patterns onto an eardrum in a temporal sequence; (b) capturing, with a camera, a first set of images of the eardrum while the eardrum is illuminated by the first set of illumination patterns; (c) calculating a g-component of the first set of images; and (d) calculating, based on the g-component, instructions for a display screen to display an image of a middle ear and of the eardrum; wherein (1) each illumination pattern in the first set of illumination patterns is (A) a spatially periodic pattern of illumination, and (B) is shifted in phase relative to at least one other illumination pattern in the first set of illumination patterns, and (2) the middle ear is medial to the eardrum. In some cases, the first set of illumination patterns are projected one pattern at a time, in the temporal sequence. In some cases, the method further comprises displaying the image of the eardrum and of the middle ear, according to the instructions. In some cases, each illumination pattern in the first set of illumination patterns has a spatial frequency of k spatial periods per millimeter of eardrum, where $0.2 \leq k \leq 4$. In some cases, each respective illumination pattern, in the first set of illumination patterns, is projected by regions of pixels in a projector in such a manner that, for each respective region of pixels: (a) the entire respective region is either in an ON binary state or an OFF binary state at each given time while the respective pattern is projected; and (b) the number of pixels in the respective region is less than $1 \times 10^{-4}$ of the total number of pixels in the projector and more than $1 \times 10^{-6}$ of the total number of pixels in the projector. In some cases, the image of the middle ear and of the eardrum includes an image of a stapes and an incus, which stapes and incus are in the middle ear. In some cases, each illumination pattern in the first set of illumination patterns differs in spatial frequency from at least one other illumination pattern in the first set of illumination patterns. In some cases, each illumination pattern in the first set of illumination patterns, when emitted by a projector, varies in intensity as a periodic function of spatial position along a spatial axis. In some cases: (a) a first illumination pattern in the first set of illumination patterns, when emitted by a projector, varies in intensity as a periodic function of spatial position along a first spatial axis; (b) a second illumination pattern in the first set of illumination patterns, when emitted by a projector, varies in intensity as a periodic function of spatial position along a second spatial axis; and (c) the first and second axes are perpendicular to each other. In some cases, the method further comprises: (a) projecting a second set of illumination patterns onto the eardrum in a temporal sequence; (b) capturing a second set of images while the eardrum is illuminated by the second set of illumination patterns; (c) calculating a third set of images, by subtracting a fraction of the g-component from each image in the second set of images, respectively, and (d) calculating, based on the third set of images, a 3D map of the eardrum; wherein each illumination pattern in the second set of illumination patterns (i) is a spatially periodic pattern of illumination, and (ii) is shifted in phase relative to at least one other illumination pattern in the second set of illumination patterns. Each of the cases described above in this paragraph is an example of the method described in the first sentence of this paragraph, and is also an example of an embodiment of this invention that may be combined with other embodiments of this invention.

In some implementations, this invention is a method comprising: (a) projecting a first set of illumination patterns onto an eardrum in a temporal sequence; (b) capturing, with a camera, a first set of images of the eardrum while the eardrum is illuminated by the first set of illumination patterns; (c) calculating a g-component of the first set of images; and (d) calculating, based on the g-component, instructions for a display screen to display an image of a middle ear and of the eardrum; wherein (i) each illumination pattern in the first set of illumination patterns is a spatial pattern of illumination, and (ii) the middle ear is medial to the eardrum. In some cases, the method further comprises displaying the image of the middle ear and of the eardrum, according to the instructions. In some cases, the method further comprises: (a) projecting a second set of illumination patterns onto the eardrum in a temporal sequence, each pattern in the second set of illumination patterns being a spatial pattern of illumination; (b) capturing a second set of images while the eardrum is illuminated by the second set of illumination patterns; (c) calculating a third set of images, by subtracting a fraction of the g-component from each image in the second set of images, respectively, and (d) calculating, based on the third set of images, a 3D map of the eardrum. Each of the cases described above in this paragraph is an example of the method described in the first sentence of this paragraph, and is also an example of an embodiment of this invention that may be combined with other embodiments of this invention.

In some implementations, this invention is an otoscope comprising: (a) a projector; (b) a camera; and (c) one or more computers that are programmed (i) to control the projector in such a manner that the projector projects a first set of illumination patterns onto an eardrum in a temporal sequence, (ii) to control the camera in such a manner that the camera captures a first set of images of the eardrum while the eardrum is illuminated by the first set of illumination patterns, (iii) to calculate a g-component of the first set of images; and (iv) to calculate, based on the g-component, instructions for a display screen to display an image of a middle ear and of the eardrum; wherein each illumination pattern in the first set of illumination patterns is (A) a spatially periodic pattern of illumination, and (B) is shifted in phase relative to at least one other illumination pattern in the first set of illumination patterns. In some cases, the image of the middle ear and of the eardrum includes an image of a stapes and of an incus, which stapes and incus are in the middle ear. In some cases, each illumination pattern in the first set of illumination patterns has a spatial frequency of k spatial periods per millimeter of eardrum, where $0.2 \leq k \leq 4$. In some cases, each respective illumination pattern in the first set of illumination patterns differs in spatial frequency from at least one other illumination pattern in the first set of illumination patterns. In some cases: (a) a first illumination pattern, in the first set of illumination patterns, is a periodic function of spatial position along a first spatial axis; (b) a second illumination pattern, in the first set of illumination patterns, is a periodic function of spatial position along a second spatial axis; and (c) the first and second axes are perpendicular to each other. In some cases, each illumination pattern in the first set of illumination patterns is a sinusoidal spatial pattern of illumination. In some cases, the one or more computers are programmed: (a) to cause the projector to project a second set of illumination patterns onto the eardrum in a temporal sequence; (b) to cause the camera to capture a second set of images while the eardrum is illuminated by the second set of illumination patterns; (c) to calculate a third set of images, by subtracting a fraction of the g-component from each image in the second set of images, respectively, and (d) to calculate, based on the third set of images, a 3D map of the eardrum; wherein each illumination pattern in the second set of illumination patterns (i) is a spatially periodic pattern of illumination, and (ii) is shifted in phase relative to at least one other illumination pattern in the second set of illumination patterns.

Each of the cases described above in this paragraph is an example of the otoscope described in the first sentence of this paragraph, and is also an example of an embodiment of this invention that may be combined with other embodiments of this invention.

Each description herein of any method or apparatus of this invention describes a non-limiting example of this invention. This invention is not limited to those examples, and may be implemented in other ways.

Each description herein of any prototype of this invention describes a non-limiting example of this invention. This invention is not limited to those examples, and may be implemented in other ways.

Each description herein of any implementation, embodiment or case of this invention (or any use scenario for this invention) describes a non-limiting example of this invention. This invention is not limited to those examples, and may be implemented in other ways.

Each Figure that illustrates any feature of this invention shows a non-limiting example of this invention. This invention is not limited to those examples, and may be implemented in other ways.

The Provisional Application does not limit the scope of this invention. The Provisional Application describes non-limiting examples of this invention, which examples are in addition to—and not in limitation of—the implementations of this invention that are described in the main part of this document. For example, if any feature described in the Provisional Application is different from, or in addition to, the features described in the main part of this document, this additional or different feature of the Provisional Application does not limit any implementation of this invention described in the main part of this document, but instead merely describes another example of this invention. As used herein, the "main part of this document" means this entire document (including any drawings listed in the Brief Description of Drawings above and any software file listed in the Computer Program Listing section above), except that the "main part of this document" does not include any document that is incorporated by reference herein.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the implementations (including hardware, hardware components, methods, processes, steps, software, algorithms, features, or technology) that are described or incorporated by reference herein.

What is claimed is:

1. A method comprising:
   (a) projecting a set of illumination patterns onto an eardrum in a temporal sequence;
   (b) capturing, with a camera, a set of images of the eardrum while the eardrum is illuminated by the set of illumination patterns;
   (c) calculating a g-component of the set of images; and
   (d) calculating, based on the g-component, instructions for a display screen to display an image of a middle ear and of the eardrum;

wherein
   (i) the middle ear is medial to the eardrum, and
   (ii) each specific illumination pattern in the set of illumination patterns
      (A) is a spatially periodic pattern of illumination,
      (B) is shifted in phase relative to at least one other illumination pattern in the set of illumination patterns, and
      (C) is projected by regions of pixels in a projector in such a manner that, for each given region in the regions of pixels
         (I) the entire given region is either in an ON binary state or an OFF binary state at each time while the specific pattern is projected, and
         (II) the number of pixels in the given region is less than $1 \times 10^{-4}$ of the total number of pixels in the projector and more than $1 \times 10^{-6}$ of the total number of pixels in the projector.

2. A method comprising:
   (a) projecting a first set of illumination patterns onto an eardrum in a temporal sequence;
   (b) capturing, with a camera, a first set of images of the eardrum while the eardrum is illuminated by the first set of illumination patterns;
   (c) calculating a g-component of the first set of images; and
   (d) calculating, based on the g-component, instructions for a display screen to display an image of a middle ear and of the eardrum;
wherein
   (i) each illumination pattern in the first set of illumination patterns
      (A) is a spatially periodic pattern of illumination, and
      (B) is shifted in phase relative to at least one other illumination pattern in the first set of illumination patterns,
   (ii) the middle ear is medial to the eardrum,
   (iii) the method further comprises
      (A) projecting a second set of illumination patterns onto the eardrum in a temporal sequence,
      (B) capturing a second set of images while the eardrum is illuminated by the second set of illumination patterns,
      (C) calculating a third set of images, by subtracting a fraction of the g-component from each image in the second set of images, and
      (D) calculating, based on the third set of images, a 3D map of the eardrum, and
   (iv) each illumination pattern in the second set of illumination patterns
      (A) is a spatially periodic pattern of illumination, and
      (B) is shifted in phase relative to at least one other illumination pattern in the second set of illumination patterns.

3. A method comprising:
   (a) projecting a first set of illumination patterns onto an eardrum in a temporal sequence;
   (b) capturing, with a camera, a first set of images of the eardrum while the eardrum is illuminated by the first set of illumination patterns;
   (c) calculating a g-component of the first set of images; and
   (d) calculating, based on the g-component, instructions for a display screen to display an image of a middle ear and of the eardrum;

wherein
- (i) each illumination pattern in the first set of illumination patterns is a spatial pattern of illumination,
- (ii) the middle ear is medial to the eardrum, and
- (iii) the method further comprises
    - (A) projecting a second set of illumination patterns onto the eardrum in a temporal sequence, each pattern in the second set of illumination patterns being a spatial pattern of illumination,
    - (B) capturing a second set of images while the eardrum is illuminated by the second set of illumination patterns,
    - (C) calculating a third set of images, by subtracting a fraction of the g-component from each image in the second set of images, and
    - (D) calculating, based on the third set of images, a 3D map of the eardrum.

4. An otoscope comprising:
- (a) a projector;
- (b) a camera; and
- (c) one or more computers that are programmed
    - (i) to control the projector in such a manner that the projector projects a first set of illumination patterns onto an eardrum in a temporal sequence,
    - (ii) to control the camera in such a manner that the camera captures a first set of images of the eardrum while the eardrum is illuminated by the first set of illumination patterns,
    - (iii) to calculate a g-component of the first set of images, and
    - (iv) to calculate, based on the g-component, instructions for a display screen to display an image of a middle ear and of the eardrum,
    - (v) to cause the projector to project a second set of illumination patterns onto the eardrum in a temporal sequence,
    - (vi) to cause the camera to capture a second set of images while the eardrum is illuminated by the second set of illumination patterns,
    - (vii) to calculate a third set of images, by subtracting a fraction of the g-component from each image in the second set of images, and
    - (viii) to calculate, based on the third set of images, a 3D map of the eardrum;

wherein
- (1) each illumination pattern in the first set of illumination patterns is a spatially periodic pattern of illumination and is shifted in phase relative to at least one other illumination pattern in the first set of illumination patterns, and
- (2) each illumination pattern in the second set of illumination patterns is a spatially periodic pattern of illumination and is shifted in phase relative to at least one other illumination pattern in the second set of illumination patterns.

* * * * *